United States Patent
Tsushima et al.

(10) Patent No.: US 10,137,069 B2
(45) Date of Patent: Nov. 27, 2018

(54) SKIN COSMETIC COMPOSITION, ANTIBACTERIAL AGENT FOR SKIN COSMETIC, AND METHOD FOR ENHANCING ANTIBACTERIAL EFFECT OF DIOL COMPOUND

(71) Applicant: ADEKA CORPORATION, Tokyo (JP)

(72) Inventors: Yasuhiro Tsushima, Tokyo (JP); Hiroshi Suzuki, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 162 days.

(21) Appl. No.: 15/119,031

(22) PCT Filed: Dec. 16, 2014

(86) PCT No.: PCT/JP2014/083201
§ 371 (c)(1),
(2) Date: Aug. 15, 2016

(87) PCT Pub. No.: WO2015/125392
PCT Pub. Date: Aug. 27, 2015

(65) Prior Publication Data
US 2016/0354291 A1 Dec. 8, 2016

(30) Foreign Application Priority Data

Feb. 24, 2014 (JP) ................................. 2014-032974

(51) Int. Cl.
| | | |
|---|---|---|
| *A61K 8/34* | (2006.01) | |
| *A61K 8/44* | (2006.01) | |
| *A61K 8/49* | (2006.01) | |
| *A61K 8/55* | (2006.01) | |
| *A61K 8/60* | (2006.01) | |
| *A61K 8/365* | (2006.01) | |
| *A61Q 17/00* | (2006.01) | |
| *A61Q 19/00* | (2006.01) | |
| *A61K 8/33* | (2006.01) | |

(52) U.S. Cl.
CPC ................ *A61K 8/345* (2013.01); *A61K 8/33* (2013.01); *A61K 8/34* (2013.01); *A61K 8/365* (2013.01); *A61K 8/44* (2013.01); *A61K 8/498* (2013.01); *A61K 8/55* (2013.01); *A61K 8/60* (2013.01); *A61Q 17/005* (2013.01); *A61Q 19/00* (2013.01)

(58) Field of Classification Search
CPC .......... A61K 8/345; A61K 8/365; A61K 8/44; A61K 8/60; A61K 8/55; A61K 8/498; A61Q 19/00; A61Q 17/005
USPC .......................................................... 514/23
See application file for complete search history.

(56) References Cited

U.S. PATENT DOCUMENTS 7,985,724 B2 * 7/2011 Inoue ..................... C11D 1/662
510/238

FOREIGN PATENT DOCUMENTS

| | | | |
|---|---|---|---|
| JP | 2005-170878 | | 6/2005 |
| JP | 2007-16018 | | 1/2007 |
| JP | 2007-161651 | | 6/2007 |
| JP | 2011-173808 | | 9/2011 |
| JP | 2011173808 | * | 9/2011 |
| WO | 2014/191258 | | 12/2014 |

OTHER PUBLICATIONS

Extended European Search Report dated Jul. 3, 2017 in corresponding European Application No. 14883082.1.
Qian et al., "Antibacterial activity of xantho-oligosaccharide cleaved from xanthan against phytopathogenic *Xanthomonas campestris* pv. *campestris*", Process Biochemistry, 41(7):1582-1588 (2006).
International Search Report dated Mar. 31, 2015 in corresponding International (PCT) Application PCT/JP2014/083201.

* cited by examiner

*Primary Examiner* — Yih-Horng Shiao
(74) *Attorney, Agent, or Firm* — Wenderoth, Lind & Ponack, L.L.P.

(57) ABSTRACT

The present invention provides a skin cosmetic composition including a component (A) which is either one or both of hexyl glyceryl ether and cyclohexyl glyceryl ether, a component (B) which is either one or both of 1,2-propanediol and 1,3-propanediol, and a component (C) such as citric acid, an antibacterial agent including components (A), (B) and (C) and a method for enhancing an antibacterial effect of the component (A).

6 Claims, No Drawings

SKIN COSMETIC COMPOSITION, ANTIBACTERIAL AGENT FOR SKIN COSMETIC, AND METHOD FOR ENHANCING ANTIBACTERIAL EFFECT OF DIOL COMPOUND

TECHNICAL FIELD

This invention relates to a cosmetic for skin which demonstrates high safety with respect to human skin and good antibacterial effect, an antibacterial agent for a skin cosmetic, and a method for enhancing antibacterial effect of a diol compound.

BACKGROUND ART

Antibacterial agents are usually used for cosmetics, detergents, etc. for antiseptic reasons. Parabens are most often used as such antibacterial agents. Although parabens have low toxicity, their drawback is that the usage concentration range thereof is limited due to high skin irritation; therefore, the usage concentration of parabens in cosmetics is restricted to 1% or less. Further, in recent years, the number of people exhibiting an allergic reaction to parabens has been increasing. Since people exhibiting the allergic reaction are sensitive to parabens even at extremely low concentrations thereof, demand has grown for cosmetics that do not include parabens. However, cosmetics using no antibacterial agents have poor stability in storage and are difficult to manage as commercial products, and therefore demand has risen for antibacterial agents which are highly safe to the human body.

Accordingly, diol compounds such as alkanediols and alkyl glyceryl ethers and compounds obtained by adding an alkylene oxide to such diol compounds are known to be used as antibacterial agents (for example, see Patent Documents 1 to 3). These compounds, while demonstrating good performance as antibacterial agents, are characterized by high safety to the human body as compared with the parabens.

CITATION LIST

Patent Document

[Patent Document 1] Japanese Patent Application Publication No. 2005-170878.
[Patent Document 2] Japanese Patent Application Publication No. 2007-016018.
[Patent Document 3] Japanese Patent Application Publication No. 2007-161651.

SUMMARY OF INVENTION

Technical Problem

Meanwhile, although such diol compounds demonstrate high safety to the human body, the antibacterial effect thereof in cosmetics of certain types or composition can be inferior to that of parabens, and the market requires further improvement in antibacterial effect with respect to a wide variety of bacteria. Therefore, it is an objective of the present invention to provide a skin cosmetic composition which is very safe to the human body and exhibits strong antibacterial effect, and also to provide an antibacterial agent for a skin cosmetic, and a method for enhancing the antibacterial effects of a diol compound.

Solution to Problem

The inventors have conducted a comprehensive study and found a blend which is safe to the human body and also demonstrates high antibacterial effect. This finding led to the creation of the present invention. The present invention provides a skin cosmetic composition comprising: a component (A) which is either one or both of hexyl glyceryl ether and cyclohexyl glyceryl ether, a component (B) which is either one or both of 1,2-propanediol and 1,3-propanediol, and a component (C) which is one or more of the group consisting of citric acid, lactic acid, hydroxyethylethylenediaminetriacetic acid, hydroxyethyliminodiacetic acid, dihydroxyethylglycine, gluconic acid, phytic acid, pentetic acid, etidronic acid, tartaric acid, and salts thereof, and gluconolactone. The present invention also relates to an antibacterial agent for a skin cosmetic comprising the component (A), the component (B), and the component (C), and also to a method for enhancing the antibacterial effect of the component (A) in the skin cosmetic, the method comprising adding the component (A), the component (B), and the component (C) to the skin cosmetic.

Advantageous Effects of Invention

The skin cosmetic composition according to the invention is very safe to the human body and exhibits high antibacterial effects. Further, the skin cosmetic composition of the invention causes little irritation of the skin and excellent feeling in use.

DESCRIPTION OF EMBODIMENTS

The component (A) used in the present invention may use either one of the hexyl glyceryl ether represented by Formula (1) below or the cyclohexyl glyceryl ether represented by Formula (2) below, or a mixture of the two components.

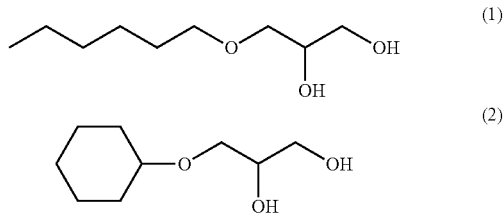

These compounds may be manufactured by any well-known method, for example, by a method of conducting a dehydrogenation condensation reaction of hexanol and glycerin, a method of conducting a dehydrochlorination or dehydrobromination reaction of hexyl chloride or hexyl bromide and glycerin, a method of conducting a dehydrochlorination reaction of hexanol and 1-chloro-2,3-propanediol, a method of reacting hexanol with epichlorohydrin and then hydrolyzing the obtained hexyl glycidyl ether, a method of reacting hexanol with glycidol, and a method of conducting a dehydrochlorination reaction of hexanol and allyl chloride, then oxidizing with hydrogen peroxide, or the like, and hydrolyzing the obtained hexyl glycidyl ether. In the reaction using glycerin, a high-purity product can be obtained by a method of conducting the abovementioned reaction by using a product of glycerin esterification with a lower fatty acid and removing the fatty acid by saponification after the completion of the reaction, or a method of conducting the abovementioned reaction by using a partial ketalization product of glycerin and removing the ketal after the completion of the reaction. Among these methods, the method of reacting hexanol with epichlorohydrin and then hydrolyzing the obtained hexyl glycidyl ether is preferred because industrial production can be easily performed at low cost. Further, cyclohexyl glyceryl ether may be produced in the same manner as described above by replacing hexanol with cyclohexanol as a starting material.

In hexyl glyceryl ether and cyclohexyl glyceryl ether, glycerin is bound by an ether bond to a hydrocarbon group having carbon atoms because good antibacterial effect cannot be obtained with compounds in which glycerin is bound by an ether bond to a hydrocarbon group having 5 or fewer carbon atoms. Meanwhile, compounds in which glycerin is bound by an ether bond to a hydrocarbon group having 7 or more carbon atoms can cause strong irritation of the skin.

The component (B) used in the present invention is 1,2-propanediol (propylene glycol) and 1,3-propanediol, and these components may be used individually or at the same time. Where tripropylene glycol or polypropylene glycol is used, good antibacterial effects cannot be obtained. Further, 1,2-propanediol and 1,3-propanediol cause less irritation than other polyhydric alcohols and excel in safety and good feeling in use as a cosmetic product. Structures of those two compounds cause practically no difference in performance. However, it is preferred that 1,2-propanediol be used because it is readily available and suitable for general use.

The component (C) of the present invention is selected from citric acid, lactic acid, hydroxyethylethylenediaminetriacetic acid, hydroxyethyliminodiacetic acid, dihydroxyethylglycine, gluconic acid, phytic acid, pentetic acid, etidronic acid, tartaric acid, and salts thereof, and gluconolactone. One or two or more compounds selected from this group may be used. The component (C) having a form of an acid may be used in the form of an acid, or may be used in the form of a salt upon full or partial neutralization. Examples of the salts include sodium salts, potassium salts, and ammonium salts.

The component (C) can be generally classified into hydroxycarboxylic acids and phosphoric acids, but the classified structures cause practically no difference in performance. Among these, citric acid, etidronic acid, phytic acid, and salts thereof, which are generally used, are preferred, citric acid, etidronic acid, and salts thereof are more preferred, and citric acid and salts thereof are most preferred.

The cosmetic composition of the present invention comprises the component (A), the component (B), and the component (C), and when each of these components is composed of a plurality of components (for example, when the component (A) is composed of hexyl glyceryl ether and cyclohexyl glyceryl ether), the total amount thereof is the respective component amount.

The component (A) is known to have an antibacterial effect, but where the component (B) and component (C) are included, the antibacterial effect is greatly improved as compared with that of the component (A) alone. For this reason, a composition comprising the component (A), component (B), and component (C) effectively acts as an antibacterial agent. Since this antibacterial agent causes little irritation to the skin and has excellent feeling in use, the antibacterial agent can be described as being unprecedented and can be used for various applications. Meanwhile, the antibacterial agent is preferably used for cosmetic applications in which these properties are most sought. Where either one of the component (B) and the component (C) is not compounded, no improvement of the antibacterial effect can be expected.

The ratio of the components is not particularly defined, but in order to demonstrate good antibacterial effect, it is preferred that the component (B) be contained at 1 part by mass to 30 parts by mass and the component (C) be contained at 0.05 parts by mass to 10 parts by mass with respect to 1 part by mass of the component (A), and it is more preferred that the component (B) be contained at 2 parts by mass to 20 parts by mass and the component (C) be contained at 0.1 parts by mass to 5 parts by mass with respect to 1 part by mass of the component (A). The abovementioned compounding ratios are also applicable to the compounding ratios of components in the antibacterial agent for a skin cosmetic of the present invention and to the compounding ratios of components in the method for enhancing antibacterial effects of the component (A) in skin cosmetics.

The amount of components (A) to (C) in the skin cosmetic composition of the present invention is not particularly defined, but it is preferred that the component (A) be compounded at 0.01% by mass to 3% by mass, more preferably 0.1% by mass to 2% by mass on the basis of the entire mass of the skin cosmetic composition. Where the amount thereof is less than 0.01% by mass, a high antibacterial effect may not be obtained, and where the amount is more than 3% by mass, irritation to the skin may increase or the effect corresponding to the amount added may not be obtained. Concerning the compounded amounts of the component (B) and component (C), these components are preferably compounded in amounts corresponding to the abovementioned preferred compounding ratios with respect to the compounded amount of the component (A).

When the antibacterial agent for a skin cosmetic of the present invention is added to a skin cosmetic, the components (A) to (C) may be added individually, or in the form of a composition obtained by mixing the components (A) to (C) in advance.

When the antibacterial agent for a skin cosmetic of the present invention is in a premixed form, as mentioned hereinabove, it may be a composition including a solvent such as water or an alcohol or an additive such as a surfactant in addition to the components (A) to (C). In this case, from the standpoint of handleability, it is preferred that the composition is adjusted such that the solid fraction of the antibacterial agent for a skin cosmetic becomes 30% by mass to 90% by mass, preferably 40% by mass to 70% by mass. It is also preferred that the component (A), component (B), and component (C) be compounded within the abovementioned ranges of compounding ratios of the components in the antibacterial agent for a skin cosmetic.

Depending on the type of component (A), the skin cosmetic composition of the present invention can exhibit different performances. Where the component (A) is hexyl glyceryl ether, the antibacterial effect generally tends to be higher than that with cyclohexyl glyceryl ether. On the other hand, where component (A) is cyclohexyl glyceryl ether, irritation to the human skin tends to be weaker than that with hexyl glyceryl ether. The type and compounded amount of component (A) may be selected, as appropriate, according to the type of cosmetic and the effect for which enhancement is sought.

In addition to the abovementioned essential components, the skin cosmetic composition of the present invention can include other components which are used in cosmetics, within ranges not impairing the advantageous effects of the present invention, examples of the other components including powder components, liquid oils and fats, solid oils and fats, waxes, hydrocarbons, higher fatty acids, higher alcohols, esters, silicones, anionic surfactants, cationic surfactants, amphoteric surfactants, nonionic surfactants, moisturizing agents, water-soluble polymers, sequestering agents, lower alcohols, polyhydric alcohols (excluding component (B) of the present invention), sugars, amino acids, organic amines, polymer emulsions, pH adjusting agents, skin nutrients, vitamins, and antioxidants. These other components can be used individually or two or more thereof can be combined as necessary and appropriate. In the description below, "POE" refers to "polyoxyethylene" and "POP" refers to "polyoxypropylene".

Examples of the powder components include inorganic powders (for example, talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstic acid metal salts, magnesium, silica, zeolite, barium sulfate, calcined calcium sulfate (calcined gypsum), calcium phosphate, fluoroapatites, hydroxyapatites, ceramic powders, metal soaps (for example, zinc myristate, calcium palmitate, and aluminum stearate), and boron nitride); organic powders (for example, polyamide resin powder (nylon powder), polyethylene powder, polymethyl methacrylate powder, polystyrene powder, powder of a copolymer resin of styrene and acrylic acid, benzoguanamine resin powder, polytetrafluoroethylene powder, and cellulose powder); inorganic white pigments (for example, titanium dioxide and zinc oxide); inorganic red pigments (for example, iron oxide (red iron oxide) and iron titanate); inorganic brown pigments (for example, γ-iron oxide); inorganic yellow pigments (for example, yellow iron oxide and ocher); inorganic black pigments (for example, black iron oxide and lower titanium oxide); inorganic purple pigments (for example, manganese violet and cobalt violet); inorganic green pigments (for example, chromium oxide, chromium hydroxide, and cobalt titanate); inorganic blue pigments (for example, ultramarine blue and Prussian blue); pearl pigments (for example, titanium oxide-coated mica, titanium oxide-coated bismuth oxychloride, titanium oxide-coated talc, colored titanium oxide-coated mica, bismuth oxychloride, and fish scale foil); metal powder pigments (for example, aluminum powder and copper powder); organic pigments such as zirconium, barium or aluminum lake (for example, organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404, and also Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1); and natural dyes (for example, chlorophyll and β-carotene).

Examples of the liquid fats and oils include avocado oil, camellia oil, turtle oil, macadamia nut oil, corn oil, mink oil, olive oil, rapeseed oil, egg yolk oil, sesame oil, persic oil, wheat germ oil, sasanqua oil, castor oil, linseed oil, safflower oil, cotton seed oil, perilla oil, soybean oil, peanut oil, tea seed oil, kaya oil, rice bran oil, Chinese tung oil, Japanese tung oil, jojoba oil, germ oil, and triglycerin.

Examples of the solid fats and oils include cacao butter, coconut oil, hardened coconut oil, palm oil, palm kernel oil, Japan wax kernel oil, hardened oil, Japan wax, and hardened castor oil.

Examples of the waxes include beeswax, candelilla wax, cotton wax, carnauba wax, bayberry wax, insect wax, whale wax, montan wax, rice bran wax, lanolin, kapok wax, lanolin acetate, liquid lanolin, sugarcane wax, lanolin fatty acid isopropyl, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin alcohol ether.

Examples of the hydrocarbon oils include liquid paraffin, ozokerite, squalane, pristane, paraffin, ceresin, squalene, vaseline, and microcrystalline wax.

Examples of the higher fatty acids include lauric acid, myristic acid, palmitic acid, stearic acid, behenic acid, oleic acid, undecylenic acid, tall oil fatty acid, isostearic acid, linoleic acid, linolenic acid, eicosapentaenoic acid (EPA), and docosahexaenoic acid (DHA).

Examples of the higher alcohols include straight-chain alcohols (for example, lauryl alcohol, cetyl alcohol, stearyl alcohol, behenyl alcohol, myristyl alcohol, oleyl alcohol, and cetostearyl alcohol); branched-chain alcohols (for example, monostearyl glycerin ether (batyl alcohol), 2-decyltetradecinol, lanolin alcohol, cholesterol, phytosterol, hexyl dodecanol, isostearyl alcohol, and octyldodecanol) and the like.

Examples of the ester oils include isopropyl myristate, cetyl octanoate, octyldodecyl myristate, isopropyl palmitate, butyl stearate, hexyl laurate, myristyl myristate, decyl oleate, hexyl decyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid esters, N-alkyl glycol monoisostearate, neopentyl glycol dicaprate, diisostearyl malate, glycerin di-2-heptyl undecanoate, trimethylolpropane tri-2-ethylhexanoate, trimethylolpropane triisostearate, pentaerythritol tetra-2-ethylhexanoate, glycerin tri-2-ethylhexanoate, glycerin trioctanoate, glycerin triisopalmitate, trimethylolpropane triisostearate, cetyl 2-ethylhexanoate, 2-ethylhexyl palmitate, glycerin trimyristate, glyceride tri-2-heptylundecanoate, castor oil fatty acid methyl esters, oleyl oleate, acetoglyceride, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, and 2-ethylhexyl succinate.

Examples of the silicone oils include chain polysiloxanes (for example, dimethylpolysiloxane, methylphenylpolysiloxane, and diphenylpolysiloxane); cyclic polysiloxanes (for example, octamethylcyclotetrasiloxane, decamethylcyclopentasiloxane, and dodecamethylcyclohexasiloxane); silicone resins forming a three-dimensional network structure, silicone rubbers, and various modified polysiloxanes (amino-modified polysiloxanes, polyether-modified polysiloxanes, alkyl-modified polysiloxanes, fluorine-modified polysiloxane, etc.).

Examples of the anionic surfactants include fatty acid soaps (for example, sodium laurate and sodium palmitate); salts of higher alkyl sulfuric acid esters (for example, sodium lauryl sulfate and potassium lauryl sulfate); salts of alkylether sulfuric acid esters (for example, POE-triethanolamine lauryl sulfate and POE-sodium lauryl sulfate); N-acyl sarcosinic acid (for example, sodium lauroyl sarcosine); higher fatty acid amidosulfonates (for example, sodium N-myristoyl-N-methyl taurate, sodium coconut oil fatty acid methyl taurate, and sodium lauryl methyl taurate); salts of phosphoric acid esters (POE-sodium oleyl ether phosphate, POE-stearyl ether phosphoric acid, etc.); sulfosuccinates (for example, sodium di-2-ethylhexylsulfosuccinate, sodium monolauroyl monoethanolamide polyoxyethylene sulfosuccinate, and sodium lauryl polypropylene glycol sulfosuccinate); alkylbenzene sulfonates (for example, sodium linear dodecylbenzenesulfonate, triethanolamine linear dodecylbenzenesulfonate, and linear dodecylbenzenesulfonic acid), salts of higher fatty acid ester sulfonic acid esters (for example, hardened coconut oil fatty acid glycerin sodium sulfate); N-acyl glutamates (for example, monosodium N-lauroylglutamate, disodium N-stearoylglutamate, and monosodium N-myristoyl-L-glutamate); sulfated oils (for example, Turkey Red Oil); POE-alkyl ether carboxylic acids; POE-alkyl allyl ether carboxylates; α-olefin sulfonates; higher fatty acid ester sulfonates; salts of secondary alcohol sulfuric acid esters; salts of higher fatty acid alkylol amide sulfuric acid esters; sodium lauroyl monoethanolamide succinate, ditriethanolamine N-palmitoyl aspartate; and sodium caseinate.

Examples of the cationic surfactants include alkyltrimethylammonium salts (for example, stearyltrimethylammonium chloride and lauryltrimethylammonium chloride); alkylpyridinium salts (for example, cetylpyridinium chloride); distearyldimethylammonium dialkyldimethylammonium chloride salts; poly(N,N'-dimethyl-3,5-methylene piperidinium) chloride; alkyl quaternary ammonium salts; alkyldimethylbenzylammonium salts; alkylisoquinolinium salts; dialkyl morphonium salts; POE-alkylamines; alkylamine salts; polyamine fatty acid derivatives; amyl alcohol fatty acid derivatives; benzalkonium chloride; and benzethonium chloride;

Examples of the amphoteric surfactants include imidazoline-based amphoteric surfactants (for example, 2-undecyl-N,N,N-(hydroxyethyl carboxymethyl)-2-imidazoline sodium and 2-cocoyl-2-imidazolinium hydroxide-1-carboxyethyloxy disodium salt); and betaine-based surfactants (for example, 2-heptadecyl-N-carboxymethyl-N-hydroxyethyl imidazolinium betaine, betaine lauryl dimethylaminoacetate, alkyl betaines, amidobetaines, and sulfobetaines).

Examples of the nonionic surfactants include sorbitan fatty acid esters (for example, sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate); glycerin polyglycerin fatty acids (for example, mono-cottonseed oil fatty acid glycerin, glycerin monoerucate, glycerin sesquioleate, glycerin monostearate, α,α'-glycerin oleate pyroglutamate, and glycerin monostearate malate); propylene glycol fatty acid esters (for example, propylene glycol monostearate); hardened castor oil derivatives; glycerin alkyl ethers, POE-sorbitan fatty acid esters (for example, POE-sorbitan monooleate, POE-sorbitan monostearate, POE-sorbitan monooleate, and POE-sorbitan tetraoleate), POE sorbitol fatty acid esters (for example, POE-sorbitol monolaurate, POE-sorbitol monooleate, POE-sorbitol pentaoleate, and POE-sorbitol monostearate); POE-glycerin fatty acid esters (for example, POE-glycerin monostearate, POE-glycerin monoisostearate, and POE-glycerin triisostearate); POE-fatty acid esters (for example, POE-distearate, POE-monodioleate, and ethylene glycol distearate); POE-alkyl ethers (for example, POE-lauryl ether, POE-oleyl ether, POE-stearyl ether, POE-behenyl ether, POE-2-octyldodecyl ether, and POE-cholestanol ether); Pluronic-type compounds (for example, Pluronic); POE•POP-alkyl ethers (for example, POE•POP-cetyl ether, POE•POP-2-decyltetradecyl ether, POE•POP-monobutyl ether, POE•POP-hydrogenated lanolin, and POE•POP-glycerin ether); tetra-POE•tetra-POP-ethylenediamine condensates (for example, Tetronic); POE-castor oil hardened castor oil derivatives (for example, POE-castor oil, POE-hardened castor oil, POE-hardened castor oil monoisostearate, POE-hardened castor oil triisostearate, POE-hardened castor oil monopyroglutamate monoisostearate diester, and POE-hardened castor oil maleic acid); POE-beeswax•lanolin derivatives (for example, POE-sorbitol beeswax); alkanolamides (for example, coconut oil fatty acid diethanolamide, lauric acid monoethanolamide, and fatty acid isopropanolamide); POE-propylene glycol fatty acid esters; POE-alkylamines; POE-fatty acid amides; sucrose fatty acid esters; alkylethoxydimethylamine oxide; and trioleyl phosphoric acid.

Examples of the moisturizing agent include polyethylene glycol, xylitol, sorbitol, maltitol, chondroitin sulfate, hyaluronic acid, mucoitin sulfuric acid, charonic acid, atelocollagen, cholesteryl-12-hydroxystearate, sodium lactate, bile salt, dl-pyrrolidone carboxylate, short-chain soluble collagen, diglycerin (EO) PO adduct, chestnut rose extract, yarrow extract, and sweet clover extract.

Examples of the natural water-soluble polymers include plant-based polymers (for example, gum arabic, tragacanth gum, galactan, guar gum, carob gum, karaya gum, carrageenan, pectin, agar, quince seed (quince), algae colloids (brown alga extract), starches (rice, corn, potato, and wheat), and glycyrrhizin acid); microorganism-based polymers (for example, xanthan gum, dextran, succinoglucan, pullulan, and gellan gum); animal-based polymers (for example, collagen, casein, albumin, and gelatin).

Examples of the water-soluble polymers include starch-based polymers (for example, carboxymethyl starch and methylhydroxypropyl starch); cellulose-based polymers (methyl cellulose, ethyl cellulose, methylhydroxypropyl cellulose, hydroxyethyl cellulose, sodium cellulose sulfate, hydroxypropyl cellulose, carboxymethyl cellulose, sodium carboxymethyl cellulose, crystalline cellulose, and cellulose powder); alginic acid-based polymers (for example, sodium alginate and propylene glycol alginate); vinyl polymers (for example, polyvinyl alcohol, polyvinyl methyl ether, polyvinyl pyrrolidone, and carboxyvinyl polymer); polyoxyethylene-based polymers (for example, polyoxyethylene polyoxypropylene copolymer of polyethylene glycol 20,000, 40,000, and 60,000); acrylic polymers (for example, sodium polyacrylate, polyethyl acrylate, and polyacrylamide); polyethyleneimine; and cationic polymers.

Examples of the metal ion sequestering agents include 1-hydroxyethane-1,1-diphosphonic acid, 1-hydroxyethane-1,1-diphosphonic acid tetrasodium salt, disodium edetate, trisodium edetate, tetrasodium edetate, sodium polyphosphate, sodium metaphosphate, phosphoric acid, ascorbic acid, succinic acid, and edetic acid.

Examples of the lower alcohols include ethanol, propanol, isopropanol, isobutyl alcohol, t-butyl alcohol and the like.

Examples of the polyhydric alcohols include trihydric alcohols (for example, glycerin and trimethylolpropane); tetrahydric alcohols (for example, pentaerythritol such as 1,2,5,6-hexane tetraol); pentahydric alcohols (for example, xylitol); hexahydric alcohols (for example, sorbitol and mannitol); polyhydric alcohol polymers (for example, diethylene glycol, triethylene glycol, dipropylene glycol, polypropylene glycol, tetraethylene glycol, diglycerin, polyethylene glycol, triglycerin, tetraglycerin, and polyglycerin); dihydric alcohol alkyl ethers (for example, ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, and ethylene glycol dibutyl ether); dihydric alcohol alkyl ethers (for example, diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether); dihydric alcohol ether esters (for example, ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate); glycerin monoalkyl ethers (for example, chimyl alcohol, selachyl alcohol, and batyl alcohol); sugar alcohols (for example, sorbitol, maltitol, maltotriose, mannitol sucrose, erythritol, glucose, fructose, starch degradation sugar, maltose, xylitose, and starch degradation sugar reduced alcohol); glysolid, tetrahydrofurfuryl alcohol; POE-tetrahydrofurfuryl alcohol; POP-butyl ether; POP•POE-butyl ether; tripolyoxypropylene glycerin ether; POP-glycerin ether; POP-glycerin ether phosphoric acid; POP•POE-pentaneerythritol ether; and polyglycerin.

Examples of the monosaccharides include trioses (for example, D-glyceryl aldehyde and dihydroxyacetone); tetroses (for example, D-erythrose, D-erythrulose, D-threose, and erythritol); pentaoses (for example, L-arabinose, D-xylose, L-lyxose, D-arabinose, D-ribose, D-ribulose, D-xylulose, and L-xylulose); hexyloses (for example, D-glucose, D-talose, D-psicose, D-galactose, D-fructose, L-galactose, L-mannose, and D-tagatose); heptoses (for example, aldo-heptose and heplose), octoses (for example, octulose); deoxysugar (for example, 2-deoxy-D-ribose, 6-deoxy-L-galactose, and 6-deoxy-L-mannose); amino sugars (for example, D-glucosamine, D-galactosamine, sialic acid, aminouronic acid, and muramic acid); and uronic acids (for example, D-grucuronic acid, D-mannuronic acid, L-guluronic acid, D-galacturonic acid, and L-iduronic acid).

Examples of the oligosaccharides include sucrose, gentianose, umbelliferose, lactose, planteose, isolychnoses, α,α-trehalose, raffinose, lychnoses, umbilicin, and stachyose, verbascoses.

Examples of the polysaccharides include cellulose, quince seed, chondroitin sulfate, starch, galactan, dermatan sulfate, glycogen, gum arabic, heparan sulfate, hyaluronic acid, tragacanth gum, keratan sulfate, chondroitin, xanthan gum, mucoitinsulfuric acid, guar gum, dextran, keratosulfate, locust bean gum, succinoglucan, and charonic acid.

Examples of the amino acids include neutral amino acids (for example, threonine and cysteine); and basic amino acids (for example, hydroxylysine). Examples of amino acid derivatives include sodium acyl sarcosine (sodium lauroyl sarcosine), acyl glutamate, sodium acyl β-alanine, glutathione, and pyrrolidone carboxylic acid.

Examples of organic amines include monoethanolamine, diethanolamine, triethanolamine, morpholine, triisopropanolamine, 2-amino-2-methyl-1,3-propanediol, and 2-amino-2-methyl-1-propanol.

Examples of the polymer emulsions include acrylic resin emulsions, ethyl polyacrylate emulsions, acrylic resin liquids, polyacrylic alkyl ester emulsions, polyvinyl acetate resin emulsions, and natural rubber latex.

Examples of the pH adjusting agents include buffers such as lactic acid-sodium lactate and succinic acid and sodium succinate.

Examples of the vitamins include vitamins A, B1, B2, B6, C, and E and derivatives thereof, pantothenic acid and derivatives thereof, and biotin.

Examples of the antioxidants include tocopherols, dibutyl hydroxytoluene, butyl hydroxyanisole, and gallic acid esters.

Examples of other compoundable components include antiphlogistic agents (for example, glycyrrhizic acid derivatives, glycyrrhetic acid derivatives, salicylic acid derivatives, hinokitiol, zinc oxide, and allantoin); whitening agents (for example, saxifrage extract and arbutin); various extracts (for example, cork tree bark, Japanese coptis, lithospermum, peony, swertia herb, birch, sage, loquat, carrot, aloe, mallow, iris, grape, coix, sponge gourd, lily, saffron, cnidium rhizome, ginger, hypericum, Ononis spiosa, garlic, red pepper, citrus unshiu, Japanese angelica, and seaweed); activators (for example, royal jelly, photosensitizers, and cholesterol derivatives); blood circulation accelerators (for example, nicotinic acid benzyl ester, nicotinic acid β-butoxyethyl ester, capsaicin, zingerone, cantharides tincture, ichthammol, tannic acid, α-borneol, tocopheryl nicotinate, inositol hexanicotinate, cyclandelate, cinnarizine, tolazoline, acetylcholine, verapamil, cepharanthine, and γ-oryzanol); antiseborrheic agents (for example, sulfur and thianthol); and anti-inflammatory agents (for example, tranexamic acid, thiotaurine, and hypotaurine).

The skin cosmetic composition of the present invention may be used in any cosmetic, provided that it is applied to human skin, for example, in creams, face cleansing creams, cleansing foams, cleansing creams, cleansing milks, cleansing lotions, massage creams, moisturizing creams, sunscreen creams, hand creams, lipsticks, liquid foundations, lotions, cosmetic liquids, and milks.

EXAMPLES

The present invention will be described below in greater detail on the basis of examples thereof. In the example, etc., stands for "% by mass", unless specifically indicated otherwise.

<Preparation of Test Cosmetics>

Test lotions and test creams were obtained from a lotion (Formulation 1) and a cream (Formulation 2) according to the below-described formulations and blends presented in Tables 1 and 2. A "Skin Irritation Test" was performed using the obtained test lotions and test creams. In addition, the following three strains of bacteria and two strains of fungi were added one strain at a time to each test lotion and test cream such that the number of bacteria in the obtained test lotions and test creams was $10^6$ cfu/g, followed by mixing till a homogeneous state was obtained. An "Antiseptic test" was then implemented. The five strains used for the evaluation are presented below.

(Bacteria)
*Escherichia coli* ATCC 8739
*Pseudomonas aeruginosa* NBRC13275
*Staphylococcus aureus* ATCC 6538
(Fungi)
*Candida Albicans* ATCC 10231
*Aspergillus brasiliensis* ATCC 16404

(Formulation 1: Lotion)

| | |
|---|---|
| Polyethylene glycol Polyethylene glycol (weight average molecular weight 1500) | 2.0% |
| Glycerin | 1.0% |
| Polyoxyethylene sorbitol tetraoleate (30EO) | 1.5% |
| (PEG-240/decyltetradeceth-20/HDI) copolymer | 0.8% |
| Xanthan gum | 1.0% |
| Sodium hydroxide | Appropriate amount (adjustment to pH 6.0) |
| Components (A), (B), and (C) | Compounded amounts shown in the table |
| Water | Balance |

(Formulation 2: Cream)

| | |
|---|---|
| Dimethyl polysiloxane | 8.0% |
| Triethylhexanoin | 10.0% |
| (Acrylates/alkyl acrylates (C10-30)) cross-polymer | 0.2% |
| POE (20) monostearate sorbitan | 3.0% |
| Glycerin | 2.0% |
| Sodium hydroxide | Appropriate amount (adjustment to pH 6.0) |
| Components (A), (B), and (C), etc. | Compounded amounts shown in the table |
| Water | Balance |

The below-described components were combined at the compounding ratios presented in Tables 1 and 2 and test cosmetics were produced according to the above-described compounding tables of cosmetics. The numerical values in the tables represent the compounded amount (% by mass) related to the entire cosmetic.

<Components Used in the Test>
A-1: hexyl glyceryl ether
A-2: cyclohexyl glyceryl ether
A-3: 2-ethylhexyl glyceryl ether
A-4: pentyl glyceryl ether
B-1: 1,2-propanediol
B-2: tripropylene glycol
B-3: polypropylene glycol (weight-average molecular weight 400)
C-1: citric acid
C-2: lactic acid
C-3: hydroxyethylethylenediaminetriacetic acid
C-4: hydroxyethyliminodiacetic acid
C-5: dihydroxyethylglycine
C-6: gluconic acid
C-7: gluconolactone
C-8: phytic acid
C-9: pentetic acid
C-10: etidronic acid
C-11: tartaric acid

TABLE 1

Blends 1 (example blends)

Blends (% by mass)

| | 1 | 2 | 3 | 4 | 5 | 6 | 7 | 8 | 9 | 10 | 11 | 12 | 13 |
|---|---|---|---|---|---|---|---|---|---|---|---|---|---|
| A-1 | 0.3 | 0.3 | 0.3 | 0.3 | 0.3 | 0.3 | 0.3 | 0.3 | 0.3 | 0.3 | 0.3 | | |
| A-2 | | | | | | | | | | | | 1.0 | 1.0 |
| A-3 | | | | | | | | | | | | | |
| A-4 | | | | | | | | | | | | | |
| B-1 | 5.0 | 5.0 | 5.0 | 5.0 | 5.0 | 5.0 | 5.0 | 5.0 | 5.0 | 5.0 | 5.0 | 5.0 | 5.0 |
| B-2 | | | | | | | | | | | | | |
| B-3 | | | | | | | | | | | | | |
| C-1 | 0.3 | | | | | | | | | | | 0.3 | |
| C-2 | | 1.0 | | | | | | | | | | | 1.0 |
| C-3 | | | 0.1 | | | | | | | | | | |
| C-4 | | | | 0.3 | | | | | | | | | |
| C-5 | | | | | 0.8 | | | | | | | | |
| C-6 | | | | | | 1.2 | | | | | | | |
| C-7 | | | | | | | 1.2 | | | | | | |
| C-8 | | | | | | | | 0.1 | | | | | |
| C-9 | | | | | | | | | 0.2 | | | | |
| C-10 | | | | | | | | | | 0.2 | | | |
| C-11 | | | | | | | | | | | 0.4 | | |

TABLE 2

Blends 2 (comparison example blends)

Comparative blends (% by mass)

| | 1 | 2 | 3 | 4 | 5 | 6 | 7 | 8 | 9 | 10 | 11 | 12 |
|---|---|---|---|---|---|---|---|---|---|---|---|---|
| A-1 | 0.3 | | 0.3 | | | | | | 0.3 | 0.3 | | |
| A-2 | | 1.0 | | 1.0 | | | | | | | 1.0 | 1.0 |
| A-3 | | | | | 0.2 | 0.05 | | | | | | |
| A-4 | | | | | | | 5.0 | 1.0 | | | | |
| B-1 | | 5.0 | 5.0 | 5.0 | 5.0 | | 5.0 | 5.0 | | | | |
| B-2 | | | | | | | | | 3.0 | | 3.0 | |
| B-3 | | | | | | | | | | 3.0 | | 3.0 |
| C-1 | 0.3 | 0.3 | | | 0.3 | 0.3 | 0.3 | | 0.3 | | | 0.3 |
| C-2 | | | | | | | | 0.3 | | 0.3 | 0.3 | |
| C-3 | | | | | | | | | | | | |
| C-4 | | | | | | | | | | | | |
| C-5 | | | | | | | | | | | | |
| C-6 | | | | | | | | | | | | |
| C-7 | | | | | | | | | | | | |
| C-8 | | | | | | | | | | | | |
| C-9 | | | | | | | | | | | | |
| C-10 | | | | | | | | | | | | |
| C-11 | | | | | | | | | | | | |

The skin irritation test and antiseptic test were conducted using the lotions and creams prepared according to the above-described compositions. The test methods are described below.

<Skin Irritation Test>

The lotions of the test cosmetics were applied to washed faces of 20 women monitors, and the feelings in use were evaluated according to the following criteria. The scores were averaged and ranked according to the following criteria. The results are shown in Tables 3 and 4.

(Score Criteria)
1: absolutely no irritation felt
2: slight subtle irritation felt
3: light irritation felt
4: strong irritation felt
5: irritation felt such that cosmetic not placed on cheek (Ranking)
A: score average is less than 2.0
B: score average is 2.0 or more and less than 3.0
C: score average of 3.0 or more <Antiseptic Test>

The following three strains of bacteria and two strains of fungi were added one strain at a time to each of to the obtained lotions and creams of the test cosmetics to obtain the number of bacteria of $10^6$ cfu/g, followed by mixing till a homogeneous state was obtained. The "Antiseptic test" was then implemented. The five strains used for the evaluation are presented below.

(Bacteria)
*Escherichia coli* ATCC 8739
*Pseudomonas aeruginosa* NBRC13275
*Staphylococcus aureus* ATCC 6538

The following symbols are used in the tables: (+): does not meet the criteria; (−): meets the criteria.

<Test Results>

The test results are presented below. Numerals in the Examples and Comparative Examples correspond to the numerals representing the compositions in Tables 1 and 2 above. For example, Example 1 is the lotion and cream to which the Blend 1 was added, and Comparative Example 1 is the lotion and cream to which the Comparative blend 1 was added.

TABLE 3

Test results

| | | Examples | | | | | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 | 13 |
| Lotion | E. Coli | − | − | − | − | − | − | − | − | − | − | − | − | − |
| | P. Aeruginosa | − | − | − | − | − | − | − | − | − | − | − | − | − |
| | S. Aureus | − | − | − | − | − | − | − | − | − | − | − | − | − |
| | C. Albicans | − | − | − | − | − | − | − | − | − | − | − | − | − |
| | A. Brasiliensis | − | − | − | − | − | − | − | − | − | − | − | − | − |
| Cream | E. Coil | − | − | − | − | − | − | − | − | − | − | − | − | − |
| | P. Aeruginosa | − | − | − | − | − | − | − | − | − | − | − | − | − |
| | S. Aureus | − | − | − | − | − | − | − | − | − | − | − | − | − |
| | C. Albicans | − | − | − | − | − | − | − | − | − | − | − | − | − |
| | A. Brasiliensis | − | − | − | − | − | − | − | − | − | − | − | − | − |
| Irritation test results | | A | A | A | A | A | A | A | A | A | A | A | A | A |

TABLE 4

Test results

| | | Comparative Examples | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Lotion | E. Coli | − | − | − | − | − | + | − | + | − | − | − | − |
| | P. Aeruginosa | + | + | + | − | − | + | − | + | + | + | + | + |
| | S. Aureus | − | + | − | − | − | + | − | + | − | − | + | + |
| | C. Albicans | − | + | − | − | − | + | − | + | − | − | + | + |
| | A. Brasiliensis | + | + | + | − | − | + | + | + | + | + | + | + |
| Cream | E. Coil | − | + | − | − | − | + | − | + | − | − | + | + |
| | P. Aeruginosa | + | + | + | − | − | + | − | + | + | + | + | + |
| | S. Aureus | + | + | + | + | + | + | − | + | + | + | + | + |
| | C. Albicans | − | + | − | − | − | + | − | + | − | − | + | + |
| | A. Brasiliensis | + | + | + | − | − | + | + | + | + | + | + | + |
| Irritation test results | | A | A | A | A | C | A | C | A | A | A | A | A |

(Fungi)
*Candida Albicans* ATCC 10231
*Aspergillus brasiliensis* ATCC 16404

The lotions and creams to which the bacteria were added were manipulated in accordance with the preservation efficacy test method of Japanese Pharmacopoeia. More specifically, the lotions and creams to which the bacteria have been added were stored in a thermostat at 25° C., changes in the number of bacteria after 2 weeks and 4 weeks were examined, and the antiseptic efficacy was determined according to the following evaluation criteria. The results are shown in Tables 3 and 4.

(Evaluation Criteria)

Bacteria: the number of bacteria after 2 weeks was 0.1% or less of the number of bacteria ($10^6$ cfu/g) at the time of the addition; the number of bacteria after 4 weeks was equal to or less than that after 2 weeks.

Fungi: the number of fungi after 2 weeks was equal to or less than the number of fungi ($10^6$ cfu/g) at the time of the addition; the number of fungi after 4 weeks was equal to or less than that after 2 weeks.

The invention claimed is:

1. A skin cosmetic composition comprising: a component (A) which is either hexyl glyceryl ether or both of hexyl glyceryl ether and cyclohexyl glyceryl ether, a component (B) which is either one or both of 1,2-propanediol and 1,3-propanediol, and a component (C) which is one or more compound(s) selected from the group consisting of lactic acid, hydroxyethylethylenediaminetriacetic acid, hydroxyethyliminodiacetic acid, dihydroxyethylglycine, gluconic acid, phytic acid, pentetic acid, etidronic acid, tartaric acid, salts thereof, and gluconolactone, wherein an amount of the component (B) is 1 part by mass to 30 parts by mass and an amount of the component (C) is 0.05 parts by mass to 10 parts by mass with respect to 1 part by mass of the component (A).

2. The skin cosmetic composition of claim 1, wherein an amount of the component (A) is 0.01% by mass to 3% by mass on the basis of the entire mass of the skin cosmetic composition.

3. An antibacterial agent for a skin cosmetic, comprising: a component (A) which is either hexyl glyceryl ether or both of hexyl glyceryl ether and cyclohexyl glyceryl ether, a component (B) which is either one or both of 1,2-propanediol and 1,3-propanediol, and a component (C) which is one or more compound(s) selected from the group consisting of lactic acid, hydroxyethylethylenediaminetriacetic acid, hydroxyethyliminodiacetic acid, dihydroxyethylglycine, gluconic acid, phytic acid, pentetic acid, etidronic acid, tartaric acid, salts thereof, and gluconolactone, wherein an amount of the component (B) is 1 part by mass to 30 parts by mass and an amount of the component (C) is 0.05 parts by mass to 10 parts by mass with respect to 1 part by mass of the component (A).

4. A method for enhancing an antibacterial effect of a skin cosmetic, the method comprising adding to the skin cosmetic a component (A) which is either hexyl glyceryl ether or both of hexyl glyceryl ether and cyclohexyl glyceryl ether, a component (B) which is either one or both of 1,2-propanediol and 1,3-propanediol, and a component (C) which is one or more compound(s) selected from the group consisting of lactic acid, hydroxyethylethylenediaminetriacetic acid, hydroxyethyliminodiacetic acid, dihydroxyethylglycine, gluconic acid, phytic acid, pentetic acid, etidronic acid, tartaric acid, salts thereof, and gluconolactone, wherein an added amount of the component (B) is 1 part by mass to 30 parts by mass and an added amount of the component (C) is 0.05 parts by mass to 10 parts by mass with respect to 1 part by mass of the component (A).

5. The skin cosmetic composition of claim 1, wherein an amount of the component (A) is 0.1% by mass to 2% by mass on the basis of the entire mass of the skin cosmetic composition.

6. The method of claim 4, wherein an added amount of the component (A) is 0.1% by mass to 2% by mass on the basis of the entire mass of the skin cosmetic.

\* \* \* \* \*